(12) United States Patent
Hilgers et al.

(10) Patent No.: US 11,322,675 B2
(45) Date of Patent: May 3, 2022

(54) ACTUATOR DEVICE BASED ON AN ELECTROACTIVE MATERIAL

(71) Applicant: KONINKLIJKE PHILIPS N.V., Eindhoven (NL)

(72) Inventors: Achim Hilgers, Alsdorf (DE); Mark Thomas Johnson, Arendonk (BE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 469 days.

(21) Appl. No.: 16/478,248

(22) PCT Filed: Jan. 23, 2018

(86) PCT No.: PCT/EP2018/051496
§ 371 (c)(1),
(2) Date: Jul. 16, 2019

(87) PCT Pub. No.: WO2018/134421
PCT Pub. Date: Jul. 26, 2018

(65) Prior Publication Data
US 2019/0363240 A1 Nov. 28, 2019

(30) Foreign Application Priority Data

Jan. 23, 2017 (EP) ..................... 17152702

(51) Int. Cl.
| | | |
|---|---|---|
| H01L 41/04 | (2006.01) |
| A61M 16/06 | (2006.01) |
| A45D 44/22 | (2006.01) |
| A61C 17/022 | (2006.01) |
| A61M 25/01 | (2006.01) |
| H01L 41/09 | (2006.01) |
| H01L 41/193 | (2006.01) |

(52) U.S. Cl.
CPC ............ *H01L 41/042* (2013.01); *A45D 44/22* (2013.01); *A61C 17/022* (2013.01);
(Continued)

(58) Field of Classification Search
CPC . H01L 41/042; H01L 41/0926; H01L 41/193; A61M 16/0611; A61M 25/0157;
(Continued)

(56) References Cited

U.S. PATENT DOCUMENTS 7,449,818 B2    11/2008   Kato et al.
7,692,361 B2     4/2010   Kato et al.
(Continued)

FOREIGN PATENT DOCUMENTS

JP    0645665 A    2/1994
JP    09201079 A   7/1997
(Continued)

OTHER PUBLICATIONS

International Search Report From PCT/EP2018/051496 dated Apr. 20, 2018.

*Primary Examiner* — J. San Martin
(74) *Attorney, Agent, or Firm* — Schott, P.C.

(57) ABSTRACT

A device comprises a plurality of electroactive material actuator units arranged as a linear set. Data for controlling the driving of the individual units is provided on a data line, and data line connections are made between each adjacent pair of electroactive material actuator units. The electroactive material actuator units are controlled in dependence on received data from the data line. This provides a reduced complexity of the wiring when multiple actuators need to be addressed and controlled in small application environments.

17 Claims, 3 Drawing Sheets

(52) U.S. Cl.
CPC .... *A61M 16/0611* (2014.02); *A61M 25/0158* (2013.01); *H01L 41/0926* (2013.01); *H01L 41/193* (2013.01); *A61M 2205/0283* (2013.01); *A61M 2205/3569* (2013.01); *A61M 2205/50* (2013.01)

(58) Field of Classification Search
CPC .. A61M 2205/0283; A61M 2205/3569; A61M 2205/50; A45D 44/22; A61C 17/022
See application file for complete search history.

(56) References Cited

U.S. PATENT DOCUMENTS

| | | |
|---|---|---|
| 7,834,527 B2 | 11/2010 | Alvarez et al. |
| 10,312,834 B2 | 6/2019 | Van Kessel |
| 10,342,612 B2 | 7/2019 | Goshgarian et al. |
| 2006/0261709 A1 | 11/2006 | Kato et al. |
| 2007/0120444 A1 | 5/2007 | Kato et al. |
| 2010/0033835 A1 | 2/2010 | Heim et al. |
| 2013/0044049 A1 | 2/2013 | Biggs et al. |
| 2020/0328340 A1* | 10/2020 | Hilgers ................ H01L 41/042 |
| 2020/0343440 A1* | 10/2020 | Hilgers ................ H01L 41/096 |
| 2021/0050505 A1* | 2/2021 | Johnson ................ H01L 41/042 |

FOREIGN PATENT DOCUMENTS

| | | | |
|---|---|---|---|
| JP | 2006325335 A | 11/2006 | |
| RU | 2014149268 A | 7/2016 | |
| TW | 201223582 A | 6/2012 | |
| WO | 2007126452 A2 | 11/2007 | |
| WO | 2013169340 A1 | 11/2013 | |

* cited by examiner

ACTUATOR DEVICE BASED ON AN ELECTROACTIVE MATERIAL

CROSS-REFERENCE TO PRIOR APPLICATIONS

This application is the U.S. National Phase application under 35 U.S.C. § 371 of International Application No. PCT/EP2018/051496, filed on Jan. 23, 2018, which claims the benefit of EP Patent Application No. EP 17152702.1, filed on Jan. 23, 2017. These applications are hereby incorporated by reference herein.

FIELD OF THE INVENTION

This invention relates to actuator devices which make use of electroactive materials, such as electroactive polymers.

BACKGROUND OF THE INVENTION

Electroactive polymers (EAP) are an emerging class of materials within the field of electrically responsive materials. EAPs can work as sensors or actuators and can easily be manufactured into various shapes allowing easy integration into a large variety of systems.

Materials have been developed with characteristics such as actuation stress and strain which have improved significantly over the last ten years. Technology risks have been reduced to acceptable levels for product development so that EAPs are commercially and technically becoming of increasing interest. Advantages of EAPs include low power, small form factor, flexibility, noiseless operation, accuracy, the possibility of high resolution, fast response times, and cyclic actuation.

The improved performance and particular advantages of EAP material give rise to applicability to new applications.

An EAP device can be used in any application in which a small amount of movement of a component or feature is desired, based on electric actuation. Similarly, the technology can be used for sensing small movements.

The use of EAPs enables functions which were not possible before, or offers a big advantage over common sensor/actuator solutions, due to the combination of a relatively large deformation and force in a small volume or thin form factor, compared to common actuators. EAPs also give noiseless operation, accurate electronic control, fast response, and a large range of possible actuation frequencies, such as 0-20 kHz.

Devices using electroactive polymers can be subdivided into field-driven and ionic-driven materials.

Examples of field-driven EAPs are dielectric elastomers, electrostrictive polymers (such as PVDF based relaxor polymers or polyurethanes) and liquid crystal elastomers (LCE).

Examples of ionic-driven EAPs are conjugated polymers, carbon nanotube (CNT) polymer composites and Ionic Polymer Metal Composites (IPMC).

Field-driven EAP's are actuated by an electric field through direct electromechanical coupling, while the actuation mechanism for ionic EAP's involves the diffusion of ions. Both classes have multiple family members, each having their own advantages and disadvantages.

FIGS. 1 and 2 show two possible operating modes for an EAP device.

The device comprises an electroactive polymer layer 14 sandwiched between electrodes 10, 12 on opposite sides of the electroactive polymer layer 14.

FIG. 1 shows a device which is not clamped. A voltage is used to cause the electroactive polymer layer to expand in all directions as shown.

FIG. 2 shows a device which is designed so that the expansion arises only in one direction. The device is supported by a carrier layer 16. A voltage is used to cause the electroactive polymer layer to curve or bow.

The nature of this movement for example arises from the interaction between the active layer which expands when actuated, and the passive carrier layer. To obtain the asymmetric curving around an axis as shown, molecular orientation (film stretching) may for example be applied, forcing the movement in one direction.

The expansion in one direction may result from the asymmetry in the electroactive polymer, or it may result from asymmetry in the properties of the carrier layer, or a combination of both.

Due to their inherent small form factor, electroactive polymers are well suited to be used in applications were multiple functions need to be realized, and thus where multiple actuators are need. For example, in certain applications, an array of actuators can be useful, for instance in positioning systems and controlled topology surfaces.

However, a basic interconnection solution would require at least one wire or cable to be connected to each of the actuators and additionally one (common) ground connection. The higher the number of actuators, the more complex the electrical connections become. If hundreds of actuators need to be addressed for example in a matrix like approach, this cannot easily be realized by a conventional wiring scheme, especially if small form factors such as in mobile devices or medical surgery equipment, are required.

For example, in a catheter or guide wire based device, it would be impractical to have all actuator devices individually controlled by wires emerging from the end of the device, as this would require the wires to run throughout the length of the device. In practical situations there is no space to accommodate these wires, and in addition the wires would reduce the maneuverability of the device.

Long wires are also prone to defects (breakage or short circuits) which would especially be the case if the wires were made thin.

An alternative approach which enables a reduction in connection lines is to use a matrix addressing scheme.

A passive matrix array is a simple implementation of an array driving system using only row (n rows) and column (m columns) connections. Only (n+m) drivers are required to address up to (n×m) actuators. This provides a cost effective approach which also reduces the am amount of wiring.

However, a passive matrix EAP actuator array will suffer from cross talk between adjacent actuators. When voltage is applied to actuate one actuator, the actuators around it also experience a voltage and will partially actuate, which is an unwanted effect for many applications. This means there is a best actuation contrast ratio which can be achieved. Hence, with a passive matrix addressing scheme it is not straightforward to individually address each actuator independently of the others.

The use of an active matrix for addressing arrays of electroactive polymer actuators has been contemplated, for example for electronic braille applications. An active matrix approach involves providing a switching device at each electroactive polymer actuator, at the intersection of a row conductor and a column conductor. In this way, each actuator in the array can, if desired, be individually actuated.

However, this requires a cyclic addressing sequence, so that the array of devices is not truly addressed simultaneously. There is also still a significant number of electrical connections required, for all of the rows and columns of the array.

Another issue is that each actuator and controller arrangement may require both high voltage actuator voltages, typically around 200V, and low voltage control voltages for the control electronics. This again implies additional connections to the actuator.

SUMMARY OF THE INVENTION

There is therefore a need for an addressing scheme which can address a multiplicity of EAPs whilst simultaneously providing the high and the low voltages required for operation of the system and using a reduced number of electrical connections.

It is an object of the current invention to fulfill the aforementioned need at least partially. This object is achieved at least partially by the invention as defined by the independent claims. The dependent claims provide advantageous embodiments.

According to examples in accordance with an aspect of the invention, there is provided a device comprising:
 a plurality of electroactive material actuator units arranged as a linear set, each electroactive material actuator unit comprising at least two power line terminals and at least one digital data line terminal;
 at least two power lines and a data line, wherein each electroactive material actuator unit is connected in parallel between the at least two power lines, the at least two power lines connecting to the at least two power line terminals; and
 data line connections between each adjacent pair of electroactive material actuator units of the linear set,
 wherein each electroactive material actuator unit comprises:
  an electroactive material actuator;
  a digital controller connected to the at least one data line terminal for receiving data from the data line; and
  a driver for driving the electroactive material actuator in dependence on the received data.

By "linear set" is meant that the units are connected electrically in a line. The physical configuration may however be in any desired shape, including a two dimensional array of units.

This device makes use of a single data line to address multiple actuators. The actuator units are also powered by common power lines (they are in parallel between those power lines) so that a small set of power lines and data lines are used to control all actuator units. There may be a single data line which connects to all units in parallel, or there may be a daisy chain connection of the data line between the units. The data line forms a digital bus.

This design enables a small form factor for the overall device with a small number of electrical connections which need to be routed to and from the actuator units.

In one example, each electroactive material actuator unit may further comprise a power unit, wherein the power unit comprises a power converter for deriving a first power supply for the controller and a second power supply for the driver from the signal on one of the at least two power lines. This design enables only two power lines; a high power line and a common reference such as ground. The high power line signal is then used to derive a relatively high voltage supply for the driver for application to the actuator and a relatively low voltage supply for the digital controller.

In another example, the device comprises three power lines, comprising a common reference power line, a controller power line and a driver power line, wherein each electroactive material actuator unit comprises three corresponding power line terminals. In this case, the circuitry at each unit can be simplified, by supplying two different power supplies to the units.

In one set of examples, each electroactive material actuator unit comprises a data line in terminal and a data line out terminal, wherein the data line connections are between the data line out terminal of one electroactive material actuator unit and the data line in terminal of the next electroactive material actuator unit.

This forms a daisy chain connection of the units. The data line connects to a first one of the units, and the signal is then passed (after local modification) from one unit to the next.

An overall device controller is used for providing power on the power lines and a data signal on the data line. The device controller may in this set of examples be adapted to provide a data signal which comprises a set of data words in series, each data word associated with a respective one of the electroactive material actuator units, wherein the controller of each electroactive material actuator unit is adapted to strip off the associated data word. Thus, as the data signal is passed along the daisy chain, the word to be read is stripped off. In this way, each unit performs the same action, of reading a word in a particular position of the data signal (e.g. at the front) and then stripping that word off the signal. The units may thus all be of the same design, and the control of which data words reach which units is dictated by the overall device controller.

In another set of examples, each electroactive material actuator unit comprises a data line in terminal, wherein the data line connections are between the data line in terminal of one electroactive material actuator unit and the data line in terminal of the next electroactive material actuator unit. In this case, the data line in terminals all become connected in parallel to the same data line.

A device controller is again used for providing power on the power lines and a data signal on the data line. The device controller may in this set of examples be adapted to provide a data signal which comprises a set of identification words and data words in series, each identification word associated with a respective one of the electroactive material actuator units, wherein the controller of each electroactive material actuator unit is adapted to recognize its own associated identification word and read the associated data word. Thus, all units receive the same data signal, but different portions are linked to different identities. This means each unit needs to know its own identity so that the relevant data word can be identified within the data signal.

The electroactive material actuators for example comprise electroactive polymer actuators.

Examples in accordance with another aspect of the invention provide a method of actuating a device which comprises:
 a plurality of electroactive material actuator units arranged as a linear set, each electroactive material actuator unit comprising at least two power line terminals and at least one digital data line terminal;
 at least two power lines and a data line, wherein each electroactive material actuator unit is connected in parallel between the at least two power lines, the at least two power lines connecting to the at least two power line terminals; and
 data line connections between each adjacent pair of electroactive material actuator units of the linear set,
 wherein the method comprises:
  providing a power signal between the at least two power lines; and providing driving data for all of the electroactive material actuator units on the data line as a single combined data signal, and at each individual electroactive material actuator unit identifying a relevant portion of the combined data signal, and driving an electroactive material actuator of the electroactive material actuator unit in dependence on the relevant portion. The identification of the relevant portion of the combined data signal can be done using a digital controller such as the one of any of the devices claimed.

This method enables a shared data line to be used for all units, as well as shared power lines.

At each electroactive material actuator unit, a first power supply may be derived for a local controller and a second power supply may be derived for a local driver from the signal on one of the at least two power lines.

In this way, the number of external power lines is kept to a minimum.

In one set of examples, each electroactive material actuator unit comprises a data line in terminal and a data line out terminal, wherein the data line connections are between the data line out terminal of one electroactive material actuator unit and the data line in terminal of the next electroactive material actuator unit. The method may then comprise:

providing a data signal which comprises a set of data words in series, each data word associated with a respective one of the electroactive material actuator units; and at each electroactive material actuator unit, stripping off the associated data word.

In another set of examples, each electroactive material actuator unit comprises a data line in terminal, wherein the data line connections are between the data line in terminal of one electroactive material actuator unit and the data line in terminal of the next electroactive material actuator unit. The method may then comprise:

providing a data signal which comprises a set of identification words and data words in series, each identification word associated with a respective one of the electroactive material actuator units;

at each electroactive material actuator unit, recognizing its own associated identification word and reading the associated data word.

The method steps may be implemented at least in part by software. The invention provides for a computer program (product) comprising computer readable code stored on, or storable on a computer readable medium, or downloadable from a communications network, which code, when executed on a computer, can cause or causes execution of the steps of any one of the methods as claimed. The method of the invention can thus be implemented in software that is capable of controlling a controller and driver, possibly including a signal generator, for driving a device as claimed. The controller and/or main controller can comprise a processor and a memory, the memory having stored therein the computer program and the processor being arranged for executing the computer program product. Part of the computer program can be stored and operated at the controller of each acutator unit. Optionally the device can include user input and/or output devices and related interfaces for operating the device either automatically or by hand.

All features for the method and their advantages can be translated into features of the computer program or controller by adaptation of the controller or computer program product. The processor can be a semiconductor processor such as a central processing unit etc. The memory can be a RAM or ROM memory of any kind which can be accessed by the processor. The computer readable medium can be a memory as defined herein before and this may be e.g. CD, DVD Blue Ray or harddisk type memory. Alternatively it may be a solid state memory such as comprised in SD, Flash or USB type memory sticks or cards. The computer readable medium can also be a communications network such as LAN, WAN or local network or the like from which the program can be downloaded.

BRIEF DESCRIPTION OF THE DRAWINGS

Examples of the invention will now be described in detail with reference to the accompanying drawings, in which.

DETAILED DESCRIPTION OF THE EMBODIMENTS

The invention provides a device (and operating method for the device) which comprises a plurality of electroactive material actuator units arranged as a linear set. Data for controlling the driving of the individual units is provided on a data line, and data line connections are made between each adjacent pair of electroactive material actuator units. The electroactive material actuator units are controlled in dependence on received data from the data line.

The invention provides a reduced complexity of the wiring when multiple actuators need to be addressed and controlled in small application environments.

Figure 1:
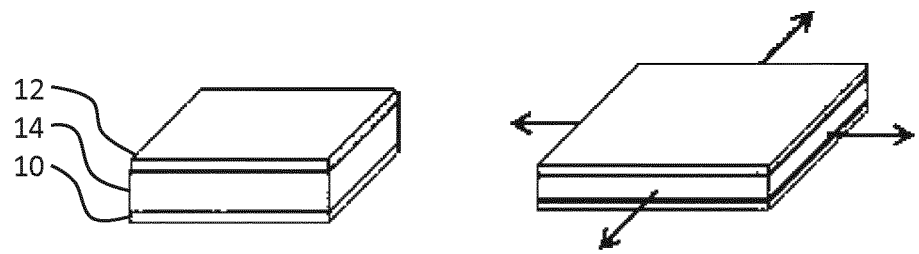
FIG. 1 shows a known electroactive polymer device which is not clamped.
Figure 2:
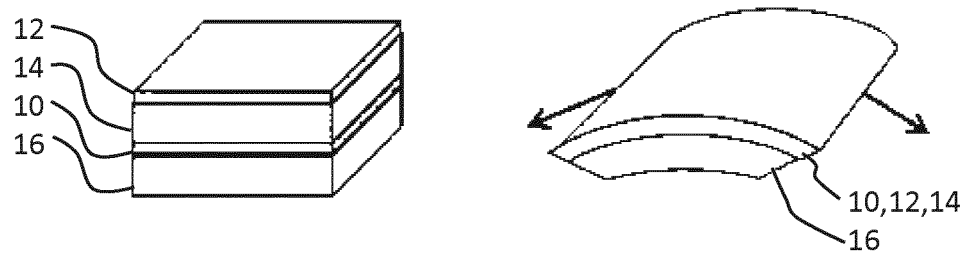
FIG. 2 shows a known electroactive polymer device which is constrained by a backing layer.
Figure 3:
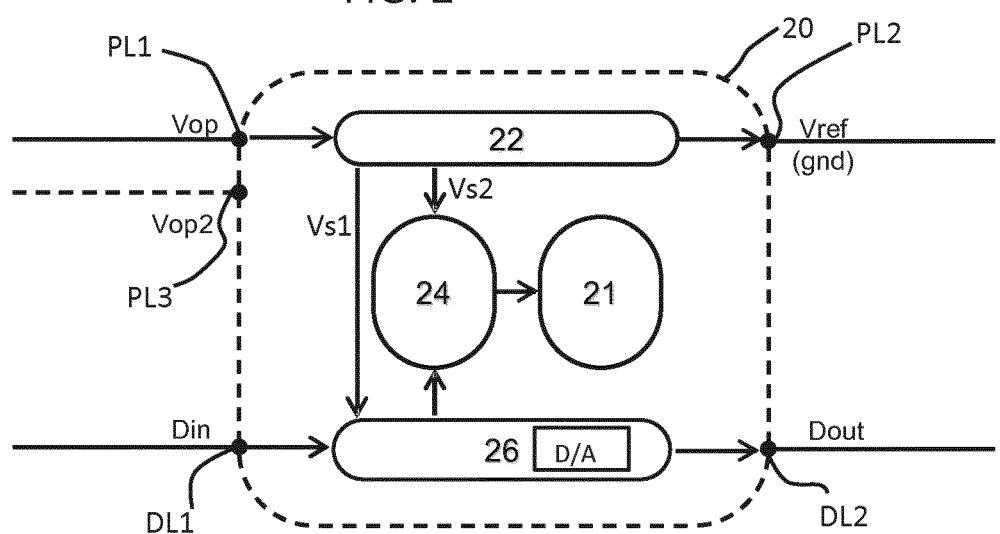
FIG. 3 shows a first example of an electroactive material actuator unit.

FIG. 3 shows a first example of an electroactive material actuator unit 20. Multiple such units are intended to form an overall device, with the units arranged as a linear set (as will be explained below). Each electroactive material actuator unit 20 comprises at least two power line terminals PL1 and PL2 and at least one digital data line terminal DL1.

FIG. 3 shows a first power line Vop on which an operating voltage is provided, which connects to a first power line terminal PL1 of the unit 20. An optional third power line Vop2 is shown which connects to a third power line terminal PL3. A reference voltage Vref forms a second power line and connects to a second power line terminal PL2, and this may be ground. A first (data in) data line Din connects to a first data line terminal DL1, and in the example of FIG. 3, each unit 20 also has a second (data out) data line terminal DL2 which connects to a data line Dout.

The electroactive material actuator unit 20 comprises an electroactive material actuator 21. There may be one or more such actuators within each unit 20. A digital controller 26 is connected to the data line terminals for receiving data from the data line Din. It interprets driving commands, which are then used to control a driver 24 for driving the electroactive material actuator 21 in dependence on the received data.

To minimize the number of external lines needed, the example of FIG. 3 has a power unit 22. The power unit comprises a power converter for deriving a first power supply Vs1 for the controller 26 and a second power supply Vs2 for the driver 24 from the signal Vop on the first power line. By providing the power unit 22 in each unit 20, the second power supply Vop2 is not needed.

The power unit 22 may be fed by an AC or preferably a DC voltage. Depending on the voltage amplitude the power unit needs to be able to convert the input voltage into a (low) dc operation voltage for the digital logic part(s) and into a (high) dc voltage suited to operate the actuator. If a high operation voltage (Vop) is used, then the power unit only needs to down-convert the voltage, to generate the low dc operation voltage for the digital control.

The power unit thus may comprise an AC/DC converter. It may comprise a DC-DC voltage up-converter and/or a DC-DC voltage down converter. Thus, depending on the overall power signal supplied, the voltage may be increased to reach the driver supply, or decreased to reach the digital controller supply, or both (for example if an intermediate voltage is provided).

If two power supplies are provided (Vop1, Vop2 as well as the reference), the units do not need internal power conversion capability. The units need two power supplies because high voltages are needed to drive the actuator (e.g. 100V or more) whereas a low voltage (e.g. 5V) is needed to power the digital circuitry.

The first power supply (Vop) may instead deliver a medium level voltage amplitude so that a relatively low up-conversion factor is still required to reach the desired voltage Vs2 to supply the driver. The use of two power supplies results in much smaller units since no (or only small) power conversion units are required.

The unit also includes a digital-to-analogue converter which receives the digital data and derives suitable analog driving signals for the driver. In the example shown, the digital-to-analog converter is part of the controller 26. It is used to enable interpretation of the digital commands on the data line, so that the driver can be controlled to deliver a corresponding analog actuation level to the actuator.

Digital to analog converter are available as integrated circuits but also can be made in analogue electronics. A preferred solution is based on using a simple (low cost) microcontroller, for D/A conversion as well as for further processing functions.

The unit of FIG. 3 is designed for connection in a serial data chain.

Assuming only one external power supply is provided, the unit 20 needs only four electrical wires to power and control any number of units, essentially connected via a serial bus and thereby operating with serial addressing.

Two terminals are used for powering the units, and two further terminals are required for digital data in and data out. In FIG. 3, any required passive components, such as parallel capacitors at each power supply terminal, are not shown.

The powering (by the pair of lines Vop and Vref) can be realized as a parallel configuration between each unit of a set.

Figure 4:
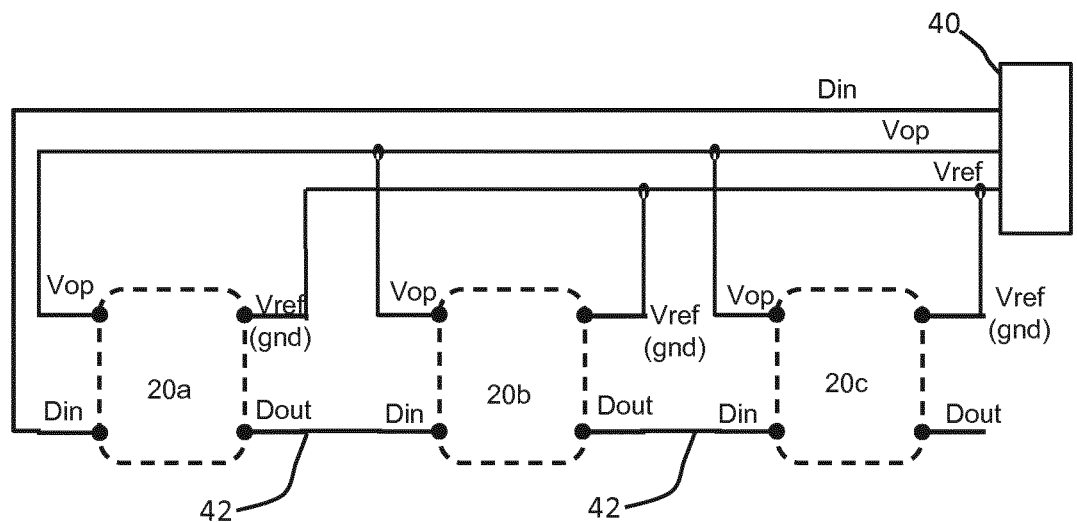
FIG. 4 shows a set of units of FIG. 3 connected together to form a device.

In the daisy chain arrangement, the digital output Dout of a preceding unit is connected to the digital input Din of the next unit. The daisy chain configuration is shown in FIG. 4 for three units 20a, 20b, 20c. It shows how all units are in parallel with respect to the power lines Vop and Vref but they are in series with respect to the data line Din.

The daisy chain arrangement defines a linear electrical connection of a set of units. The first unit 20a in the set receives its digital data stream from an overall device controller 40 which is able to generate digital data in order to control the units. The last digital output from the unit 20c at the end of the linear connection of units can be left open as shown in FIG. 4, or it may be terminated with a resistor or connected back to a digital input of the main controller 40 for example to enable a check to be made if all data has been correctly received by the units.

This connection back to the device controller 40 may also be used to enable bidirectional communication, so that the device controller can receive data generated by the units.

FIG. 4 thus shows that each electroactive material actuator unit 20a, 20b, 20c is connected in parallel between the at least two power lines Vop and Vref, and that data line connections 42 are provided between each adjacent pair of electroactive material actuator units of the set.

All of the electronics may be integrated into one chip (e.g. an application specific integrated chip, ASIC) with, if required, only a few power components connected to it. For example, most of the analogue and digital electronics may be combined and integrated in an ASIC with only limited passive components (e.g. inductors and capacitors) and/or active components (e.g. transistors) connected to it.

Figure 5:
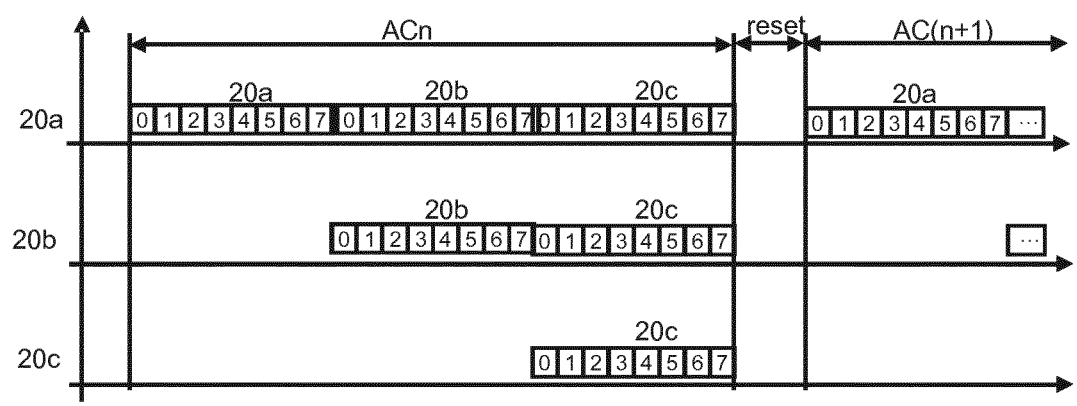
FIG. 5 shows a data signal structure for the device of FIG. 4.

Each actuator unit 20a, 20b, 20c needs to react on the reception of a digital signal stream, so that the deflection is controlled based on the digital information. FIG. 5 shows one example of a possible format of the signal to be provided to the data line for the daisy chain example of FIG. 4. Two activation cycles ACn and AC(n+1) are shown.

The resolution of the digital-to-analogue conversion needs to be defined. By way of example, an 8-bit resolution is considered. In this case, from an 8-bit word, a maximum of $2^8=256$ analogue states can be realized. A mapping between analogue control amplitude and mechanical deflection of the actuator is then defined in the driver unit of the actuator. For coding the digital information (0 or 1), many coding principles are known to people skilled in the art. For example, compression and/or security/safety algorithms may be used, as well as special starting or ending sequences.

FIG. 5 shows three 8 bit words concatenated into an overall 24-bit data signal. The first 8 bits are intended for the first unit 20a, the next 8 bits are intended for the next unit 20b and the last 8 bits are intended for the final unit 20c.

The digital data of all units is thus sent on the digital data line in a serial manner. The data is packaged by the main controller 40, and connected to the first unit 20a in the set.

The main controller 40 takes each 8-bit word for each unit and arranges them in such a way that they are written one after the other. The digital data stream starts with the 8 bits of the first unit, adds to it the 8 bits of the second unit and so on.

Thus, more generally, the total bit stream consists of 8×n bits for n units. The 24 bit words of the overall bit stream are for example separated by a 'reset' period, for example a longer low state (0) or a longer high state (1) or a specially defined bit sequence (although this may be at the expense of a reduced number of possible analogue states).

When the whole data signal is sent on the data line (i.e. digital bus), the first unit 20a reads the first 8 bits, and reduces the whole data signal by these 8 bits by stripping them off. It sends away only the remaining signal (without the first 8 bits). This is shown as the second line in FIG. 5.

The second unit 20b then reads the first 8-bit word and then strips off 8 bits from the data signal, to leave the signal shown in the bottom row of FIG. 5. Finally, the last unit 20c strips off the remaining 8 bits.

The whole procedure requires the knowledge in the main controller 40 of how many units need to be addressed. If any unit needs to change its actuation level, the whole data signal (for all units) is generated and sent again. If the number of units is to be changed this has to be announced to the main controller 40 of the system.

The output of the last unit 20c may be connected and read by the main controller 40 in order to check if all the data has been correctly received. In this case, a special bit sequence may for example be added to the starting bit stream (by the main controller) and/or each unit may add a bit sequence at the end of the total bit stream.

In its broadest concept, the invention provides a parallel connection of actuator units to power lines to allow the operation of high voltage driven actuators and low voltage driven digital control electronics. One or more operation voltages may be supplied externally. The actuator drive level is tuned according to digital information, serially connected to each of the units.

In the example above each unit is considered to have only one actuator. However, one unit may also consist of more than one actuator, such as a triplet of actuators (e.g. to generate a 3D movement/displacement per unit). In such a configuration the digital data stream may be adapted in such a way that multiple control words are provided, such as 3×8 bits (=24 bits) per unit, where each 8-bit word is dedicated to one of the three actuators in the unit.

The example of FIG. 4 is based on serial addressing.

Figure 6:
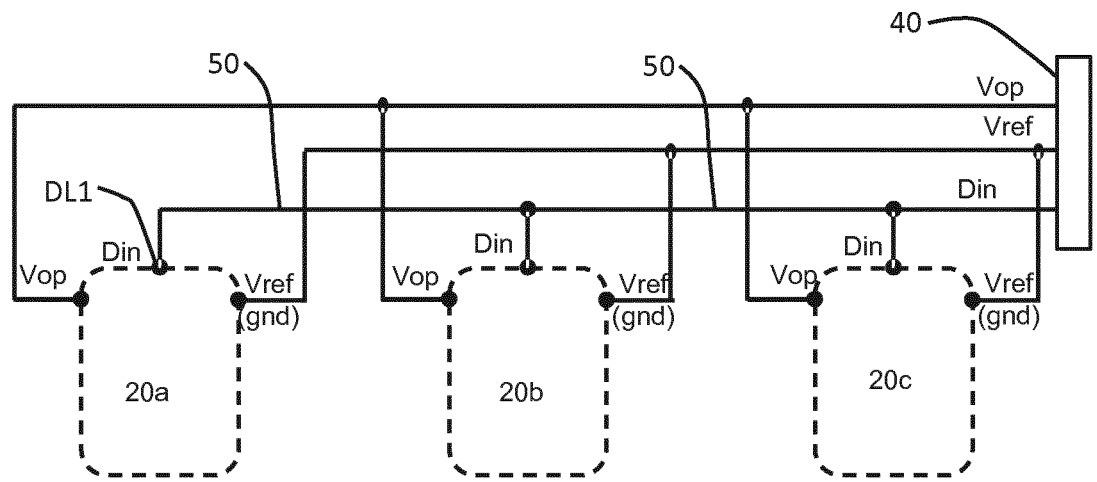
FIG. 6 shows a set of units of a second design connected together to form a device.

FIG. 6 shows an alternative which may be considered to be based on quasi-serial addressing of the actuator units.

Three electroactive material actuator units 20a, 20b, 20c are again shown. Each comprises a data line in terminal DL1 which connects to the data line Din. However, there is no data line out terminal. There are again data line connections 50, but they are between the data line in terminals of adjacent units, so that all unit are connected directly to the same data line.

In this example, the device controller 40 provides a data signal which comprises a set of identification words and data words in series, each identification word associated with a respective one of the electroactive material actuator units. The controller of each unit then recognizes its own associated identification word and reads the associated data word. In particular, in order to differentiate between the single units, it is not possible to send only data words relating to the status of a unit. In addition to this, the data signal needs to define to which unit the actual digital information belongs.

Figure 7:
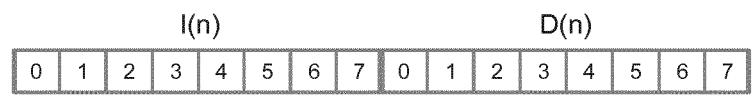
FIG. 7 shows a data signal structure for the device of FIG. 6.

FIG. 7 shows one identification word I(n) and data word D(n) pair.

This provides a quasi-serial addressing, where each unit has its power connections (Vop and Vref) as well only one parallel digital data line Din. Quasi-serial thus means that, although the digital data line is connected in parallel to each unit, during each moment in time only one data set (address+actuation data) is sent on the bus.

The data format of FIG. 7 is prepared for each unit and sent together on the bus. With an 8-bit address resolution, up to 256 units may be addressed. If more bits are used, more units could be addressed as well. In such a system, the main controller 40 needs to have all the address information of the whole device configuration. If the original configuration is changed (by adding or taking out units), this needs to be announced in the control software.

All units listen continuously to the data line. As soon as a unit recognizes its own address, the following digital information will be interpreted as actuation information for this specific unit. Digital information can be sent continuously for all units one after each other without any specific order, or also in a specific order, so that high priority units will be addressed first or so that nearest units will be addressed first.

An alternative approach is that data could be sent only for those units (serially, one after the other, with or without priority, as mentioned before) whose status needs to be changed. In such a case, all units may be deactivated or brought into their original position, before ending the application.

Bidirectional communication is also possible as mentioned above. The system can send and receive data on one data line. For example, a unit may listen to the bus, and if no data is actually sent by any of the units, new data can be sent, giving a time multiplex solution. Other communication principles such as frequency or code multiplex solutions or others may be implemented Instead of setting the digital output terminal of the last unit as open circuit (or terminated), a ring like configuration may be used, feeding back the very last digital output to the main controller. Such feedback may for example be used for providing feedback of the current actuation (deflection) state or any other sensing information (pressure, force, etc.).

One application of interest is in catheters or guide wires. In this application, there is a very limited space for connection wires and also a requirement that multiple wires do not adversely affect the stiffness.

Figure 8:
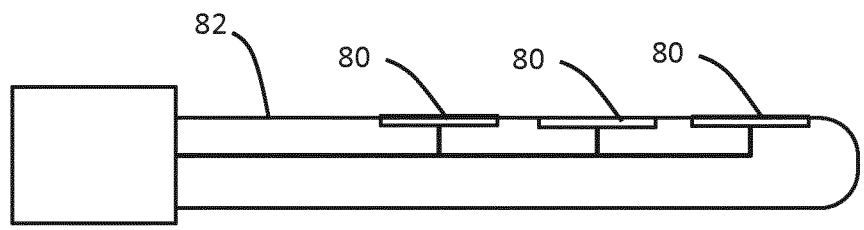
FIG. 8 shows a catheter which makes use of a set of actuators for steering control.

FIG. 8 shows a set of electroactive material actuators 80 formed along a catheter 82. Each actuator can be actuated to implement a local bending function so that the catheter can be steered. The device may in the same way be provided along or at the tip of a guide wire, such as a catheter guide wire or a stent delivery guide wire. Actuation of the device may be performed generally to induce bending, for example for steering as mentioned above, but also for scanning or motion compensation.

Electroactive material sensors may also be provided for example for measuring flow and/or pressure. For flow pressure sensing, a sag induced in a device depends on the pressure.

The electroactive material actuator preferably comprises an electroactive polymer structure for providing a mechanical actuation. The structure defines a non-actuated state and at least one actuated state (different from the non-actuated state) attainable by application of the electrical drive signal to the electroactive polymer structure. The actuator has an electrode arrangement for providing the drive signal to the EAP material. The electrode structure can be attached to the EAP material directly or with intermediate layers in between.

The EAP material layer of each unit may be sandwiched between electrodes of the electrode structure. Alternatively, electrodes can be on a same side of the EAP material. In either case, electrodes can be physically attached to the EAP material either directly without any (passive) layers in between, or indirectly with additional (passive) layers in between. However, this need not always be the case. For relaxor or permanent piezoelectric or ferroelectric EAPs, direct contact is not necessary. In the latter case, electrodes in the vicinity of the EAPs suffices as long as the electrodes can provide an electric field to the EAPs, the electroactive polymer structure will have its actuation function. The electrodes may be stretchable so that they follow the deformation of the EAP material layer.

The electrical drive signal can be a voltage signal or a current signal depending on the EAP material used (see herein below).

Materials suitable for the EAP layer are known. Electroactive polymers include, but are not limited to, the sub-classes: piezoelectric polymers, electromechanical polymers, relaxor ferroelectric polymers, electrostrictive polymers, dielectric elastomers, liquid crystal elastomers, conjugated polymers, Ionic Polymer Metal Composites, ionic gels and polymer gels.

The sub-class electrostrictive polymers includes, but is not limited to:

Polyvinylidene fluoride (PVDF), Polyvinylidene fluoride-trifluoroethylene (PVDF-TrFE), Polyvinylidene fluoride-trifluoroethylene-chlorofluoroethylene (PVDF-TrFE-CFE), Polyvinylidene fluoride-trifluoroethylene-chlorotrifluoroethylene) (PVDF-TrFE-CTFE), Polyvinylidene fluoride-hexafluoropropylene (PVDF-HFP), polyurethanes or blends thereof.

The sub-class of dielectric elastomers includes, but is not limited to:

acrylates, polyurethanes, silicones.

The sub-class conjugated polymers includes, but is not limited to:

polypyrrole, poly-3,4-ethylenedioxythiophene, poly(p-phenylene sulfide), polyanilines.

Additional passive layers may be provided for influencing the behavior of the EAP layer in response to an applied electric field.

The EAP layer may be sandwiched between electrodes. The electrodes may be stretchable so that they follow the deformation of the EAP material layer. Materials suitable for the electrodes are also known, and may for example be selected from the group consisting of thin metal films, such as gold, copper, or aluminum or organic conductors such as carbon black, carbon nanotubes, graphene, poly-aniline (PANI), poly(3,4-ethylenedioxythiophene) (PEDOT), e.g. poly(3,4-ethylenedioxythiophene) poly(styrenesulfonate) (PEDOT:PSS). Metalized polyester films may also be used, such as metalized polyethylene terephthalate (PET), for example using an aluminum coating.

The materials for the different layers will be selected for example taking account of the elastic moduli (Young's moduli) of the different layers.

Additional layers to those discussed above may be used to adapt the electrical or mechanical behavior of the device, such as additional polymer layers.

The EAP devices may be electric field driven devices or ionic devices. Ionic devices may be based on ionic polymer metal composites (IPMCs) or conjugated polymers. An ionic polymer metal composite (IPMC) is a synthetic composite nanomaterial that displays artificial muscle behavior under an applied voltage or electric field.

IPMCs are composed of an ionic polymer like Nafion or Flemion whose surfaces are chemically plated or physically coated with conductors such as platinum or gold, or carbon based electrodes. Under an applied voltage, ion migration and redistribution due to the imposed voltage across a strip of IPMCs result in a bending deformation. The polymer is a solvent swollen ion exchange polymer membrane. The field causes cations travel to cathode side together with water. This leads to reorganization of hydrophilic clusters and to polymer expansion. Strain in the cathode area leads to stress in rest of the polymer matrix resulting in bending towards the anode. Reversing the applied voltage inverts the bending.

If the plated electrodes are arranged in a non-symmetric configuration, the imposed voltage can induce all kinds of deformations such as twisting, rolling, torsioning, turning, and non-symmetric bending deformation.

The device may be used as a single actuator, or else there may be a line or array of the devices, for example to provide control of a 2D or 3D contour.

The invention can be applied in many EAP applications where an array of actuators is of interest.

In many applications the main function of the product relies on the (local) manipulation of human tissue, or the actuation of tissue contacting interfaces. In such applications EAP actuators provide unique benefits mainly because of the small form factor, the flexibility and the high energy density. Hence EAP's can be easily integrated in soft, 3D shaped and/or miniature products and interfaces. Examples of such applications are:

Skin cosmetic treatments such as skin actuation devices in the form of EAP based skin patches which apply a constant or cyclic stretch to the skin in order to tension the skin or to reduce wrinkles;

Respiratory devices with a patient interface mask which has an EAP based active cushion or seal, to provide an alternating normal pressure to the skin which reduces or prevents facial red marks;

Electric shavers with an adaptive shaving head. The height of the skin contacting surfaces can be adjusted using EAP actuators in order to influence the balance between closeness and irritation;

Oral cleaning devices such as an air floss with a dynamic nozzle actuator to improve the reach of the spray, especially in the spaces between the teeth. Alternatively, toothbrushes may be provided with activated tufts;

Consumer electronics devices or touch panels which provide local haptic feedback via an array of EAP transducers which is integrated in or near the user interface;

Catheters with a steerable tip to enable easy navigation in tortuous blood vessels. The actuator function for example controls the bending radius to implement steering, as explained above.

Another category of relevant application which benefits from EAP actuators relates to the modification of light. Optical elements such as lenses, reflective surfaces, gratings etc. can be made adaptive by shape or position adaptation using EAP actuators. Here the benefits of EAP actuators are for example the lower power consumption.

The data signals used in the system are typically generated by software running on a central controller (to generate the driving data in the form of the combined data signal) and they are read by software running locally at each EAP actuator to extract the relevant data word and process the data signal, if required.

A controller is used to run the software. The controller can be implemented in numerous ways, with software and/or hardware, to perform the various functions required. A processor is one example of a controller which employs one or more microprocessors that may be programmed using software (e.g., microcode) to perform the required functions. A controller may however be implemented with or without employing a processor, and also may be implemented as a combination of dedicated hardware to perform some functions and a processor (e.g., one or more programmed microprocessors and associated circuitry) to perform other functions.

Examples of controller components that may be employed in various embodiments of the present disclosure include, but are not limited to, conventional microprocessors, application specific integrated circuits (ASICs), and field-programmable gate arrays (FPGAs).

In various implementations, a processor or controller may be associated with one or more storage media such as volatile and non-volatile computer memory such as RAM, PROM, EPROM, and EEPROM. The storage media may be encoded with one or more programs that, when executed on one or more processors and/or controllers, perform the required functions. Various storage media may be fixed within a processor or controller or may be transportable, such that the one or more programs stored thereon can be loaded into a processor or controller.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measured cannot be used to advantage. Any reference signs in the claims should not be construed as limiting the scope.

The invention claimed is:

1. A device comprising:
    a plurality of electroactive material actuator units,
    wherein the plurality of electroactive material actuator units are arranged as a linear set,
    wherein each electroactive material actuator unit comprises at least two power line terminals and at least one digital data line terminal;
    at least two power lines,
    wherein each of the at least two power lines are connected to one of the at least two power line terminals,
    wherein each electroactive material actuator unit is connected in parallel between at least two power lines;
    a data line; and
    data line connections between each adjacent pair of electroactive material actuator units,
    wherein each electroactive material actuator unit comprises:
        an electroactive material actuator;
        a digital controller circuit,
        wherein the digital controller circuit is connected to the at least one data line terminal,
        wherein the at least one data line terminal is arranged to receive data from the data line; and
        a driver, wherein the drive is arranged to drive the electroactive material actuator in dependence on the received data.

2. The device as claimed in claim 1,
    wherein each electroactive material actuator unit comprises a power unit,
    wherein the power unit comprises a power converter,
    wherein the power converter is arranged to derive a first power supply for the digital controller circuit and a second power supply for the driver from the signal on one of the at least two power lines.

3. The device as claimed in claim 1, further comprising three power lines,
    wherein a first one of the three power lines is a common reference power line,
    wherein a second one of the three power lines is a controller power line,
    wherein a third one of the three power lines is a driver power line,
    wherein each electroactive material actuator unit comprises three corresponding power line terminals.

4. The device as claimed in claim 1,
    wherein each electroactive material actuator unit comprises a data line in terminal and a data line out terminal,
    wherein the data line connections are between the data line out terminal of one electroactive material actuator unit and the data line in terminal of the next electroactive material actuator unit.

5. The device as claimed in claim 1 further comprising a device controller circuit, wherein the device controller circuit is arranged to provide power on the power lines and a data signal on the data line.

6. The device as claimed in claim 5,
    wherein the device controller circuit is arranged adapted to provide a data signal,
    wherein the data signal comprises a set of data words in series,
    wherein each data word associated with a respective one of the electroactive material actuator units,
    wherein the controller circuit of each electroactive material actuator unit is arranged adapted to strip off the associated data word.

7. The device as claimed in claim 1,
    wherein each electroactive material actuator unit comprises a data line in terminal,
    wherein the data line connections are between the data line in terminal of one electroactive material actuator unit and the data line in terminal of the next electroactive material actuator unit.

8. The device as claimed in claim 7, further comprising a device controller circuit, wherein the device controller circuit is arranged to provide power on the power lines and a data signal on the data line.

9. The device as claimed in claim 8,
    wherein the device controller circuit is arranged adapted to provide a data signal,
    wherein the data signal comprises a set of identification words and data words in series,
    wherein each identification word is associated with a respective one of the electroactive material actuator units,
    wherein the controller circuit of each electroactive material actuator unit is arranged adapted to recognize its own associated identification word and read the associated data word.

10. A catheter comprising a device as claimed in claim 1, wherein the plurality of electroactive material actuator units are for steering control of the catheter.

11. A method of actuating a device, the device comprising:
    a plurality of electroactive material actuator units,
    wherein the plurality of electroactive material actuator units are arranged as a linear set,
    wherein each electroactive material actuator unit comprises at least two power line terminals and at least one digital data line terminal;
    at least two power lines,
    wherein each of the at least two power lines are connected to one of the at least two power line terminals,
    wherein each electroactive material actuator unit is connected in parallel between at least two power lines;
    a data line; and
    data line connections between each adjacent pair of electroactive material actuator units, the method comprising:
        providing a power signal between the at least two power lines;

providing driving data for all of the electroactive material actuator units on the data line as a single combined data signal;

identifying a relevant portion of the combined data signal at each individual electroactive material actuator unit; and driving each electroactive material actuator of the electroactive material actuator unit in dependence on the relevant portion.

12. The method as claimed in claim 11, further comprising:

deriving a first power supply for a local controller circuit at each electroactive material actuator unit; and deriving a second power supply for a local driver from the signal on one of the at least two power lines at each electroactive material actuator unit.

13. The method as claimed in claim 11, further comprising:

providing a data signal, wherein the data signal comprises a set of data words in series, wherein each data word is associated with a respective one of the electroactive material actuator units; and stripping off the associated data word at each electroactive material actuator unit, wherein each electroactive material actuator unit comprises a data line in terminal and a data line out terminal, wherein the data line connections are between the data line out terminal of one electroactive material actuator unit and the data line in terminal of the next electroactive material actuator unit.

14. The method as claimed in claim 12, further comprising:

providing a data signal, wherein the data signal comprises a set of identification words and data words in series, wherein each identification word associated with a respective one of the electroactive material actuator units;

recognizing its own associated identification word and reading the associated data word at each electroactive material actuator unit, wherein each electroactive material actuator unit comprises a data line in terminal, wherein the data line connections are between the data line in terminal of one electroactive material actuator unit and the data line in terminal of the next electroactive material actuator unit.

15. A computer program comprising computer program code stored in a non-transitory media, wherein the computer code is arranged when said program is run on a computer, to cause execution of all of the steps of the method as claimed in claim 11.

16. The method as claimed in claim 12, further comprising:

providing a data signal, wherein the data signal comprises a set of data words in series, wherein each data word is associated with a respective one of the electroactive material actuator units; and stripping off the associated data word at each electroactive material actuator unit, wherein each electroactive material actuator unit comprises a data line in terminal and a data line out terminal, wherein the data line connections are between the data line out terminal of one electroactive material actuator unit and the data line in terminal of the next electroactive material actuator unit.

17. The method as claimed in claim 13, further comprising:

providing a data signal, wherein the data signal comprises a set of identification words and data words in series, wherein each identification word associated with a respective one of the electroactive material actuator units;

recognizing its own associated identification word and reading the associated data word at each electroactive material actuator unit, wherein each electroactive material actuator unit comprises a data line in terminal, wherein the data line connections are between the data line in terminal of one electroactive material actuator unit and the data line in terminal of the next electroactive material actuator unit.

* * * * *